(12) United States Patent
Kamihara

(10) Patent No.: US 8,081,314 B2
(45) Date of Patent: Dec. 20, 2011

(54) VARIABLE SPECTROSCOPY ELEMENT, SPECTROSCOPY APPARATUS, AND ENDOSCOPE SYSTEM

(75) Inventor: Yasuhiro Kamihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 367 days.

(21) Appl. No.: 12/524,796

(22) PCT Filed: Jan. 29, 2008

(86) PCT No.: PCT/JP2008/051274
§ 371 (c)(1),
(2), (4) Date: Jul. 28, 2009

(87) PCT Pub. No.: WO2008/093664
PCT Pub. Date: Aug. 7, 2008

(65) Prior Publication Data
US 2010/0004511 A1    Jan. 7, 2010

(30) Foreign Application Priority Data
Jan. 31, 2007    (JP) .................................. 2007-021560

(51) Int. Cl.
*G01B 9/02* (2006.01)
(52) U.S. Cl. ........................................ 356/454; 359/578
(58) Field of Classification Search .................. 356/452, 356/454, 456, 506; 359/578
See application file for complete search history.

(56) References Cited

U.S. PATENT DOCUMENTS

| 6,822,779 | B2 * | 11/2004 | Chi | ............................. | 359/290 |
| 7,961,335 | B2 * | 6/2011 | Matsumoto | ................... | 356/519 |

FOREIGN PATENT DOCUMENTS

| JP | 01-094312 | 4/1989 |
| JP | 2001-356002 | 12/2001 |
| JP | 2003-057438 | 2/2003 |
| JP | 2006-178320 | 7/2006 |
| JP | 2006-187598 | 7/2006 |

* cited by examiner

*Primary Examiner* — Tarifur Chowdhury
*Assistant Examiner* — Jonathan Hansen
(74) *Attorney, Agent, or Firm* — Scully, Scott, Murphy & Presser, P.C.

(57) ABSTRACT

Desired spectral characteristics are achieved while achieving reduced size and decreased noise, and detecting the distance between optical substrates with superior precision. Provided is a variable spectroscopy element (1) including optical coating layers (3) provided on opposing surfaces, which face each other, of first and second optical substrates (4a, 4b) that face each other with a gap therebetween; an actuator (4c) that changes the gap between the first and second optical substrates (4a, 4b); a first sensor portion (6a) provided on the first optical substrate (4a), for detecting the gap between the first and second optical substrates (4a, 4b); and a second sensor portion (6b) provided on the second optical substrate (4b) so as to oppose the first sensor portion (6a), for detecting the gap between the first and second optical substrates (4a, 4b), wherein the numbers of the first and second sensor electrodes (6a, 6b) differ.

13 Claims, 11 Drawing Sheets

VARIABLE SPECTROSCOPY ELEMENT, SPECTROSCOPY APPARATUS, AND ENDOSCOPE SYSTEM

TECHNICAL FIELD

The present invention relates to a variable spectroscopy element, a spectroscopy apparatus, and an endoscope system.

BACKGROUND ART

In a known etalon-type variable spectroscopy element, two optical substrates having optical coating layers provided on opposing surfaces thereof face each other, and a gap between these optical substrates can be varied by an actuator formed of a piezoelectric device (for example, see Patent Document 1).

This variable spectroscopy element is provided with sensor electrodes of an electrostatic capacitance sensor on the opposing surfaces of the two optical substrates, and the distance between the optical substrates is detected by the electrostatic capacitance sensor, allowing the gap to be controlled.

Patent Document 1: Japanese Unexamined Patent Application, Publication No. HEI-1-94312

DISCLOSURE OF INVENTION

In order to exhibit the capabilities of such an etalon-type variable spectroscopy element, it is necessary to accurately control the parallelism of the optical substrates, and to do so, it is desirable that the actuator have multiple degrees of freedom and that the same number of detection signals as the number of degrees of freedom of the actuator be obtained.

When the variable spectroscopy element of Patent Document 1 is disposed in an extremely small space, such as the distal end of an insertion portion of an endoscope apparatus, the size of the variable spectroscopy element itself becomes extremely small. In such a case, if a plurality of actuators and sensor electrodes are disposed, the total number of wires therefor increases, making packaging difficult, and crosstalk noise increases.

The present invention provides a variable spectroscopy element, a spectroscopy apparatus, and an endoscope system which can realize a reduction in size and decreased noise, while detecting the distance between optical substrates with superior precision, and achieving desired spectral characteristics.

A first aspect of the present invention is a variable spectroscopy element including first and second optical substrates that oppose each other with a gap therebetween; optical coating layers provided on opposing surfaces, which face each other, of the first and second optical substrates; an actuator that changes the gap between the first and second optical substrates; a first sensor portion provided on the first optical substrate for detecting the gap between the first and second optical substrates; and a second sensor portion provided on the second optical substrate so as to oppose the first sensor portion, for detecting the gap between the first and second optical substrates, wherein the numbers of the first and second sensor portions differ.

In the first aspect of the present invention described above, the number of first sensor portions may be equal to or greater than the number of degrees of freedom of the actuator, and the number of second sensor portions may be smaller than the number of first sensor portions.

In the first aspect of the present invention described above, the number of first sensor portions may be equal to the number of degrees of freedom of the actuator.

In the first aspect of the present invention described above, the number of first sensor portions may be three or more. Also, in the first aspect of the present invention described above, the first optical substrate may be secured, and the second optical substrate can be displaced by the actuator.

In the first aspect of the present invention described above, the number of second sensor portions may be one.

In the first aspect of the present invention described above, the first and second sensor portions may be sensor portions of the electrostatic capacitance type.

In the first aspect of the present invention described above, the first and second sensor portions may be sensor portions of the eddy current type.

A second aspect of the present invention is a spectroscopy apparatus including any one of the variable spectroscopy elements described above; and an image-acquisition device that captures light spectrally separated by that variable spectroscopy element.

A third aspect of the present invention is an endoscope system including the spectroscopy apparatus described above.

In the third aspect of the present invention described above, the variable spectroscopy element may be provided in an insertion portion that is inserted inside a body cavity, and the second sensor portion may be disposed farther toward the distal-end side of the insertion portion than the first substrate is.

The present invention affords an advantage in that it is possible to realize a smaller size and reduced noise, while detecting the distance between the optical substrates with superior precision, allowing desired spectral characteristics to be achieved.

BRIEF DESCRIPTION OF DRAWINGS

FIG. 1 is a longitudinal sectional view showing an image-acquisition unit provided with a variable spectroscopy element according to an embodiment of the present invention.

FIG. 2 is a diagram showing an example arrangement of reflective films and sensor electrodes, when viewing the optical substrates of the variable spectroscopy element shown in FIG. 1 from the optical-axis direction.

FIG. 3 is a diagram showing a first modification of the sensor electrodes in the variable spectroscopy element shown in FIG. 2.

FIG. 4 is a diagram showing a second modification of the sensor electrodes in the variable spectroscopy element shown in FIG. 2.

FIG. 5 is a diagram showing a third modification of the sensor electrodes in the variable spectroscopy element shown in FIG. 2.

FIG. 6 is an overall configurational diagram showing an endoscope system according to an embodiment of the present invention.

FIG. 7 is a diagram showing transmittance characteristics of a variable spectroscopy element constituting an image-acquisition unit provided in the endoscope system shown in FIG. 6.

FIG. 8 is a timing chart for explaining the operation of the endoscope system shown in FIG. 6.

FIG. 9 is a diagram showing an electrical circuit for amplifying a sensor signal in the variable spectroscopy element constituting the image-acquisition unit provided in the endoscope system shown in FIG. 6.

FIG. 10 is an overall configurational diagram showing a modification of the endoscope system shown in FIG. 6.

FIG. 11 is a longitudinal sectional view showing a distal-end light source in a light source unit disposed at the distal end of an insertion portion of the endoscope system shown in FIG. 10.

EXPLANATION OF REFERENCE SIGNS

Figure 1:
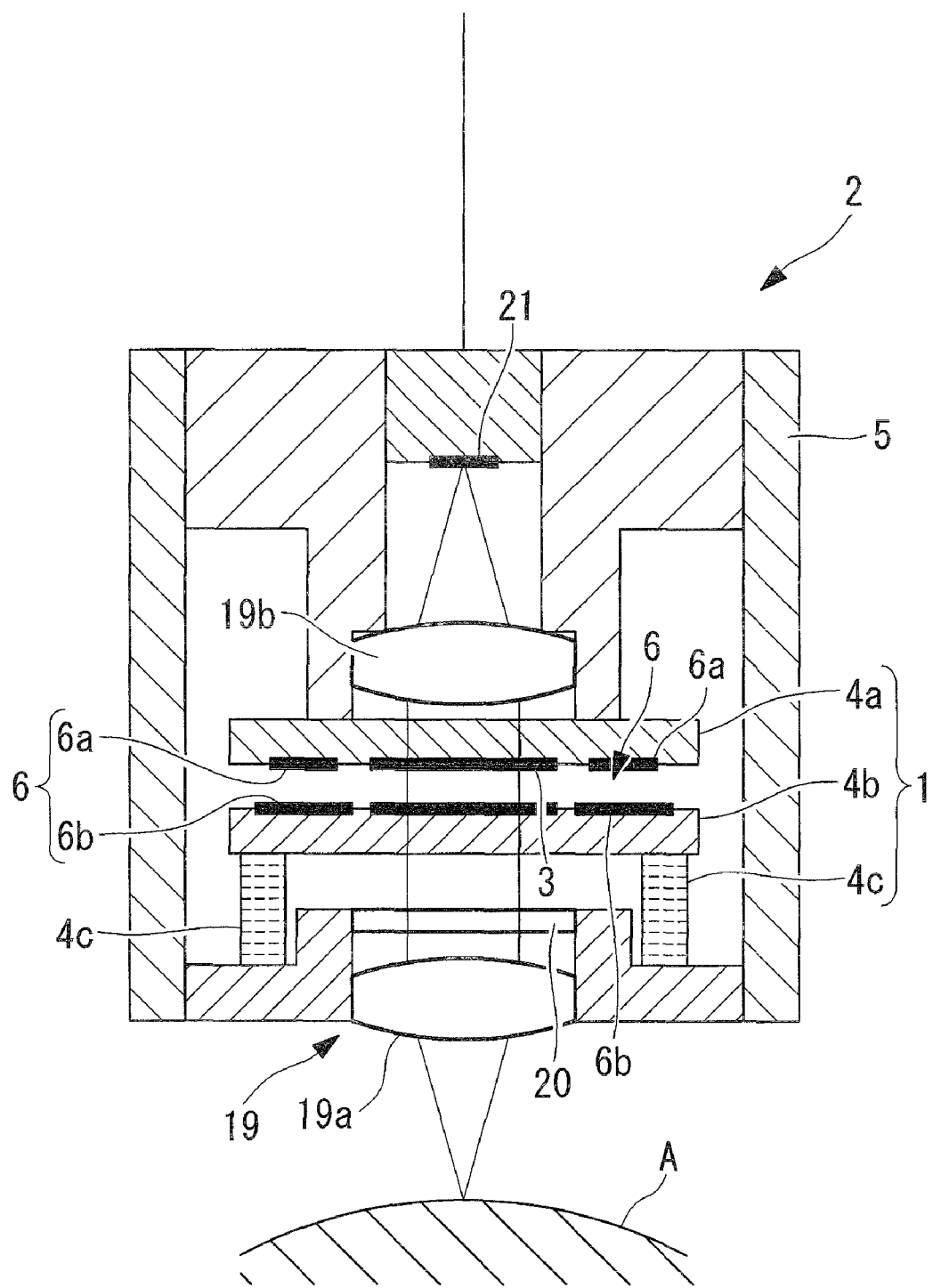
[FIG. 1]

1: variable spectroscopy element
3: reflective film (optical coating layer)
4a, 4b: optical substrate
4c: actuator
6: sensor
6a: sensor electrode (first sensor portion)
6b: sensor electrode (second sensor portion)
10: endoscope system (spectroscopy apparatus)
21: image-acquisition device

BEST MODE FOR CARRYING OUT THE INVENTION

A variable spectroscopy element 1 according to a first embodiment of the present invention will be described below with reference to FIG. 1 and FIG. 2.

As shown in FIG. 1, the variable spectroscopy element 1 according to this embodiment, which is an element provided, for example, in an image-acquisition unit 2, is an etalon-type optical filter including two circular plate-shaped optical substrates 4a and 4b disposed substantially in parallel with a gap therebetween and having reflective films (optical coating layers) 3 provided on the opposing surfaces thereof, and actuators 4c that vary the gap between the optical substrates 4a and 4b. The optical substrate 4a is directly secured to a frame member 5 constituting the image-acquisition unit 2, and the optical substrate 4b is mounted to the frame member 5 with the actuators 4c interposed therebetween.

The actuators 4c are multilayer piezoelectric devices and are provided at four locations with equal gaps therebetween in the circumferential direction around the periphery of the optical substrate 4b.

This variable spectroscopy element 1 varies the distance between the optical substrates 4a and 4b by the action of the actuators 4c. This variable spectroscopy element 1 can vary the wavelength band of light transmitted in the axial direction by varying the distance between the optical substrates 4a and 4b.

The two optical substrates 4a and 4b constituting the variable spectroscopy element 1 are provided with a sensors 6 for detecting the gap between the optical substrates 4a and 4b. The sensors 6, which is of the electrostatic capacitance type, is provided in the outer peripheral portion outside an optically effective diameter B (see FIG. 2) of the optical substrates 4a and 4b and has four sensor electrodes (first sensor portions) 6a and one sensor electrode (second sensor portion) 6b. The sensor electrodes 6a are disposed at four locations with equal gaps therebetween around the circumferential direction in the outer peripheral portion of the optical substrate 4a. The sensor electrode 6b is disposed in the outer peripheral portion of the optical substrate 4b so as to oppose all four sensor electrodes 6a. It is possible to use metal films as the sensor electrodes 6a and 6b.

Electrostatic capacitance sensors are sensors that detect the intersurface distance based on the electrostatic capacitance between the sensor electrodes 6a and 6b using the property that the electrostatic capacitance between the sensor electrodes 6a and 6b varies in inverse proportion to the intersurface distance.

Figure 2:
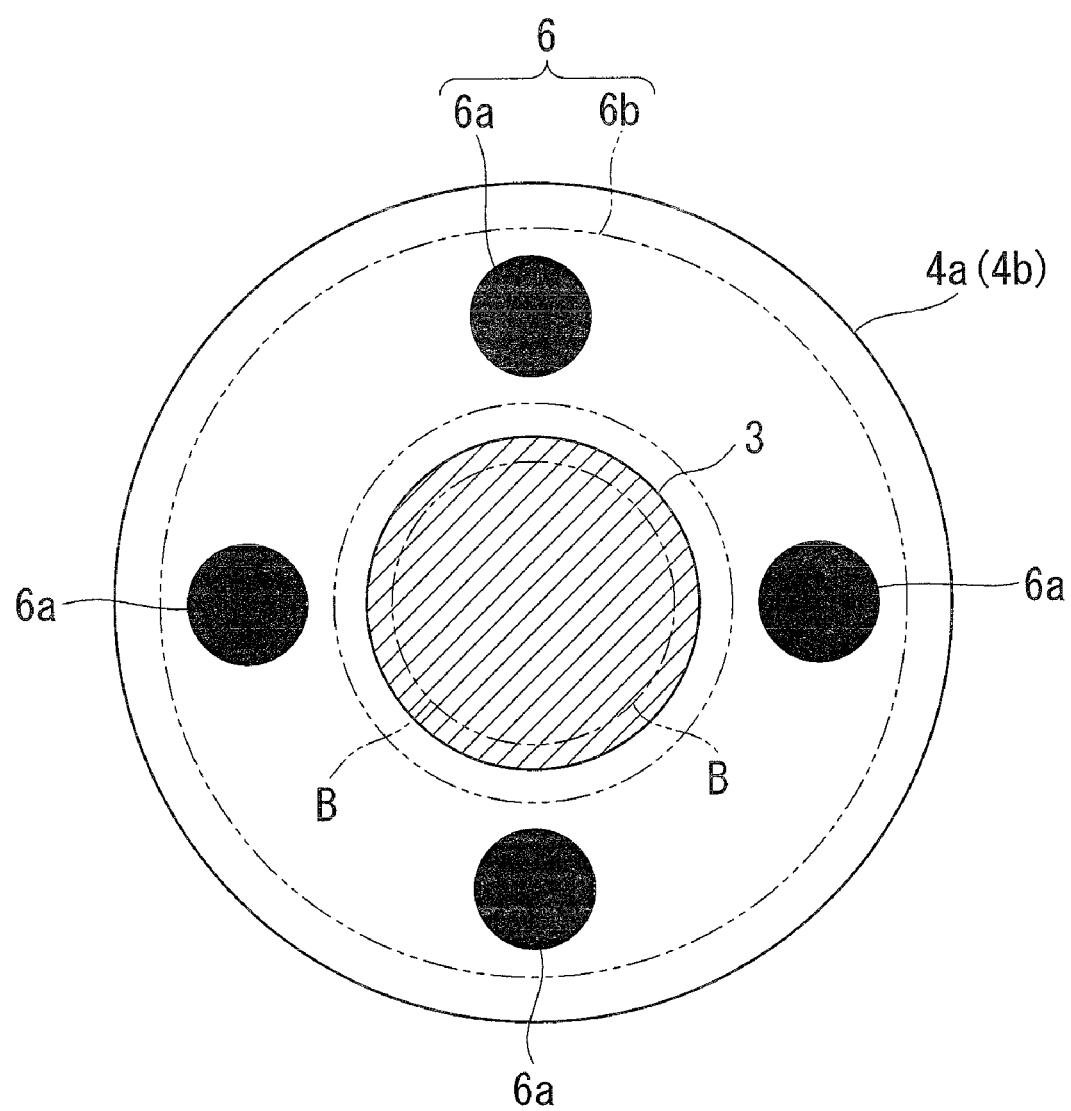
[FIG. 2]

In the variable spectroscopy element 1 according to this embodiment, as shown in FIG. 1 and FIG. 2, the sensor electrodes 6a provided on the optical substrate 4a form a circular shape, and the sensor electrode 6b provided on the optical substrate 4b forms a single ring shape so as to oppose all four of the sensor electrodes 6a provided on the optical substrate 4a with gaps therebetween in the circumferential direction. Thus, as shown in FIG. 2, the sensor electrodes 6a provided on the other optical substrate 4a are disposed inside a region where the sensor electrode 6b provided on the optical substrate 4b is projected onto the other optical substrate 4a (in the figure, the region indicated by the broken line).

In fluorescence observation, the obtained fluorescence intensity is generally weak; therefore, the transmission efficiency of the optical system is extremely important. The etalon-type variable spectroscopy element 1 achieves a high transmittance when the reflective films are parallel, but an error in adjusting the parallelism thereof abruptly reduces the transmittance. Therefore, with the variable spectroscopy element 1 used in the image-acquisition unit 2 for fluorescence observation, in order to adjust a tilt error of the two optical substrates 4a and 4b when the gap is adjusted, it is preferable to provide a plurality of the sensors 6 and to have a plurality of the actuators 4c.

With the variable spectroscopy element 1 according to this embodiment, it is possible to improve the precision in controlling the transmittance characteristic by implementing feedback control of driving signals to the actuators 4c on the basis of signals from the sensor electrodes 6a and 6b.

The operation of the thus-configured variable spectroscopy element 1 according to this embodiment will be described below.

With the variable spectroscopy element 1 according to this embodiment, light is made incident on the region of the optically effective diameter B of the two optical substrates 4a and 4b disposed substantially in parallel with a gap therebetween; thereby, only light of a wavelength defined according to the distance between the optical substrates 4a and 4b is transmitted through the two optical substrates 4a and 4b, and the remaining light is reflected. Then, the wavelength of the light transmitted through the two optical substrates 4a and 4b is changed by varying the distance between the two optical substrates 4a and 4b by operating the actuators 4c; accordingly, it is possible to spectrally separate light in a desired wavelength band to be observed from the light in other wavelength bands.

Because the sensor electrodes 6a and 6b are disposed opposite each other on the opposing surfaces of the optical substrates 4a and 4b, an electrical signal indicating the electrostatic capacitance formed between the sensor electrodes 6a and 6b is detected. The distance between the sensor electrodes 6a and 6b can be detected based on this electrical signal. Because the four sensor electrodes 6a are provided in the circumferential direction of the optical substrate 4a, and the single sensor electrode 6b opposing all of these sensor electrodes 6a is provided on the optical substrate 4b, for each pair of sensor electrodes 6a and 6b, it is possible to detect the distance between the optical substrates 4a and 4b at the corresponding positions, and by controlling the actuators 4c based on the distances detected in this way, the distances can be adjusted with superior precision while keeping the two optical substrates 4a and 4b parallel.

In this case, with the variable spectroscopy element 1 according to this embodiment, the number of sensor electrodes 6b disposed on one optical substrate 4b is smaller than the number of sensor electrodes 6a disposed on the other optical substrate 4a; therefore, it is possible to reduce the number of wires connected to the sensor electrodes 6a and 6b. Thus, packaging of the sensor electrodes 6a and 6b is facilitated, reducing the size of the variable spectroscopy element 1 and simplifying it, and in addition, individual wires are disposed at positions away from each other, which makes it possible to reduce the intrusion of crosstalk noise therebetween.

With the variable spectroscopy element 1 according to this embodiment, the number of sensor electrodes 6b provided on the optical substrate 4b which is displaced by driving the actuators 4c is smaller than the number of sensor electrodes 6a provided on the optical substrate 4a which is directly secured to the frame member 5 constituting the image-acquisition unit 2; therefore, the number of wires that move while driving the actuators 4c can be reduced, which makes it possible to reduce the incidence of noise associated with changes in capacitance between the wires.

With the variable spectroscopy element 1 according to this embodiment, even though the numbers of opposing sensor electrodes 6a and 6b are different, because the four sensor electrodes 6a provided on the optical substrate 4a oppose the sensor electrode 6b provided on the optical substrate 4b, four pairs of the sensors 6 are formed. Accordingly, it is possible to detect four electrical signals, which is the same as the number of degrees of freedom for driving, or in other words, the number of actuators 4c.

Therefore, the variable spectroscopy element 1 according to this embodiment affords an advantage in that the gap between the two optical substrates 4a and 4b can be controlled with superior precision based on the same number of electrical signals as the same number of actuators 4c, which signals indicate the electrostatic capacitance that uniquely corresponds to the distance between the two optical substrates 4a and 4b, thus enabling light of a desired wavelength band to be spectrally separated with superior precision.

In addition, in the variable spectroscopy element 1 according to this embodiment, the sensor electrode 6b is formed larger than the sensor electrodes 6a in the circumferential direction and the radial direction. Therefore, the variable spectroscopy element 1 according to this embodiment can ensure a sufficient opposing surface area to cover the surface area of the smaller sensor electrodes 6a, even though no rigorous positioning procedure is performed at the time of assembly. In other words, with the variable spectroscopy element 1 according to this embodiment, the sensor electrodes 6a provided on the other optical substrate 4a are disposed within the region where the sensor electrode 6b provided on one optical substrate 4b is projected onto the other optical substrate 4a; therefore, the electrostatic capacitance formed between the two sensor electrodes 6a and 6b does not change even if the two optical substrates 4a and 4b are assembled with a slight shift in a direction intersecting the substrate thickness direction, that is to say, the radial direction or the circumferential direction of the optical substrates 4a and 4b.

With the variable spectroscopy element 1 according to this embodiment, it is possible to adjust the distance between the two optical substrates 4a and 4b with superior precision by driving the plurality of actuators 4c. During this process, shifting of the relative positions of the two optical substrates 4a and 4b in a direction intersecting the substrate thickness direction due to individual differences among the actuators 4c is possible. In this case too, with the variable spectroscopy element 1 according to this embodiment, there is no change to the electrostatic capacitance formed between the two sensor electrodes 6a and 6b.

Therefore, the variable spectroscopy element 1 according to this embodiment affords an advantage in that an electrical signal indicating the electrostatic capacitance, which uniquely corresponds to the distance between the two optical substrates 4a and 4b, can be detected, the gap between the two optical substrates 4a and 4b can be controlled with superior precision based on this electrical signal, and it is possible to spectrally separate light in a desired wavelength band with superior precision.

In this embodiment, regarding the shapes of the sensor electrodes 6a and 6b, it is preferable that the variation of toletrances between the larger sensor electrode 6b and the smaller sensor electrodes 6a be greater in the circumferential direction than in the radial direction. The circular optical substrates 4a and 4b can be approximately positioned with superior precision in the radial direction by aligning the outer circumferential faces thereof. However, positioning of the optical substrates 4a and 4b in the circumferential direction is difficult. By increasing the variation of toletrances of the sensor electrodes 6a and 6b in the circumferential direction, as described above, even though positioning of the optical substrates 4a and 4b in the circumferential direction is performed roughly, there is no change in the electrostatic capacitance detected by the sensor electrodes 6a and 6b, which affords an advantage in that it is possible to further simplify the mounting of the variable spectroscopy element 1.

In the variable spectroscopy element 1 according to this embodiment, it is assumed that four of the sensor electrodes 6a are provided at equal intervals around the circumferential direction of one optical substrate 4a, and the single sensor electrode 6b that opposes all of these sensor electrodes 6a is provided on the other optical substrate 4b. It is not limited to this, however; any number of sensor electrodes 6a and 6b can be provided in the present invention.

Figure 3:
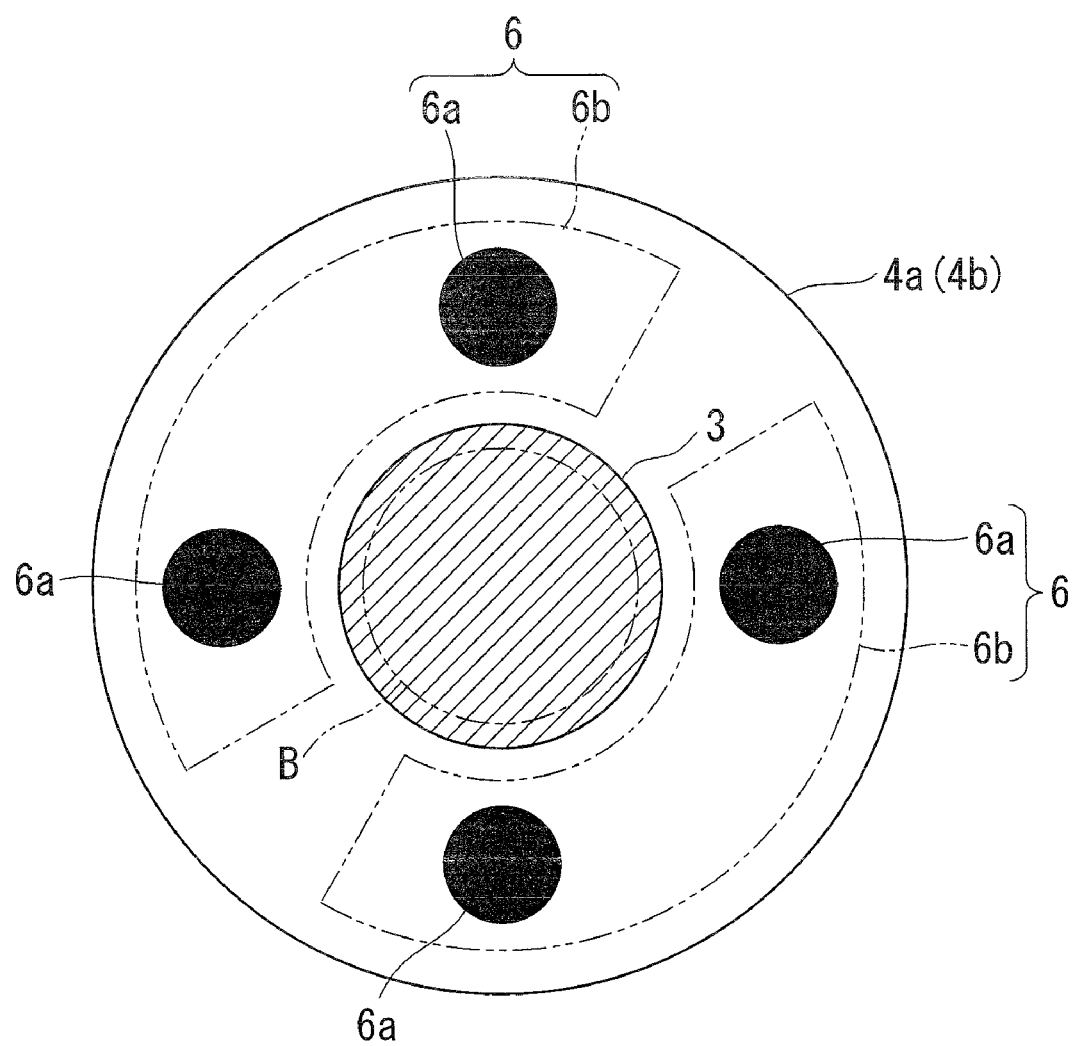
[FIG. 3]

That is, as shown in FIG. 3, for every two sensor electrodes 6a provided at intervals in the circumferential direction of one optical substrate 4a, a single sensor electrode 6b with a size that opposes both of these sensor electrodes 6a may be provided on the other optical substrate 4b.

Figure 4:
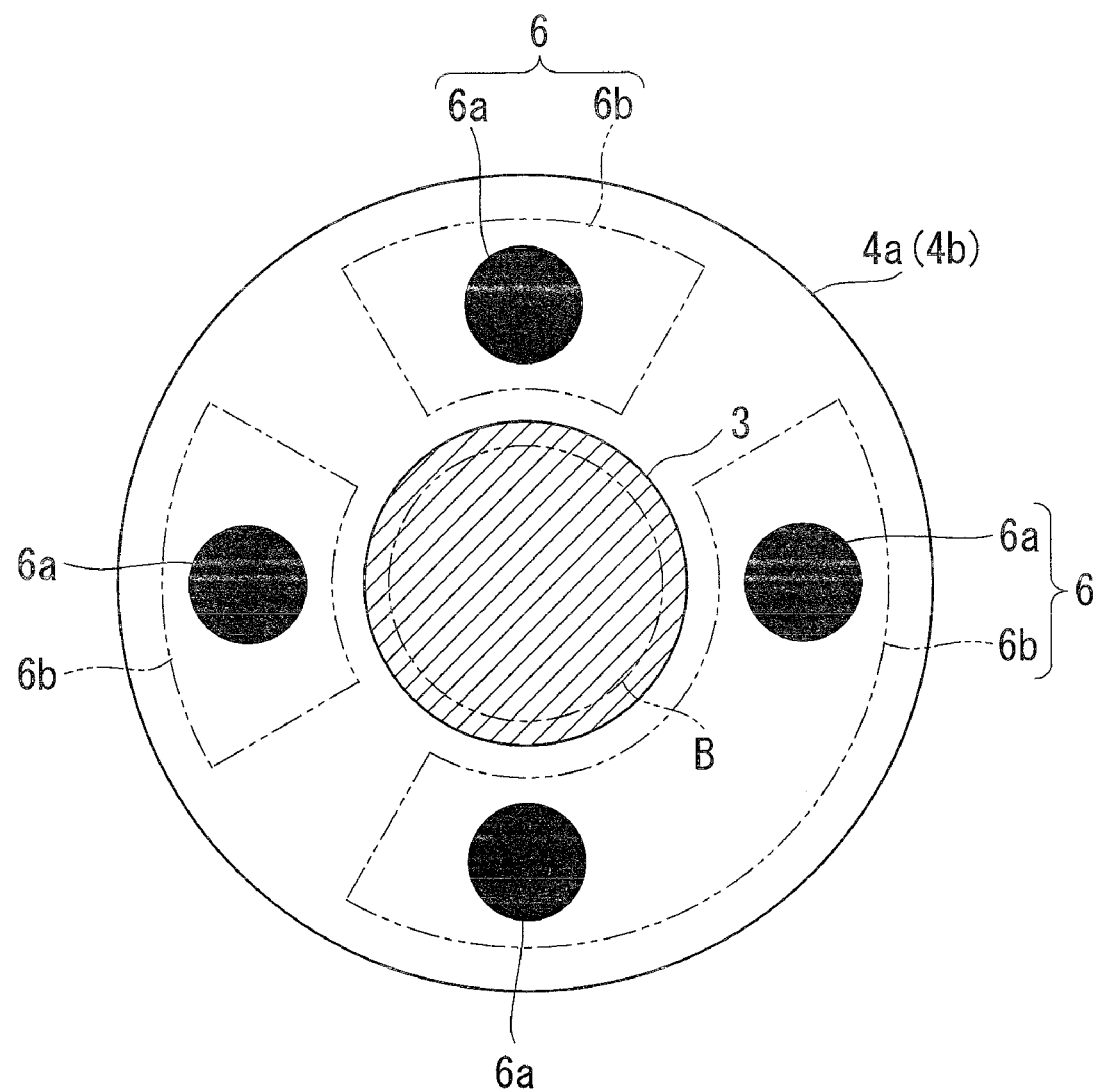
[FIG. 4]

Additionally, as shown in FIG. 4, sensor electrodes 6b that oppose some of the electrodes 6a provided on one optical substrate 4a in a one-to-one fashion may be provided on the other optical substrate 4b.

Figure 5:
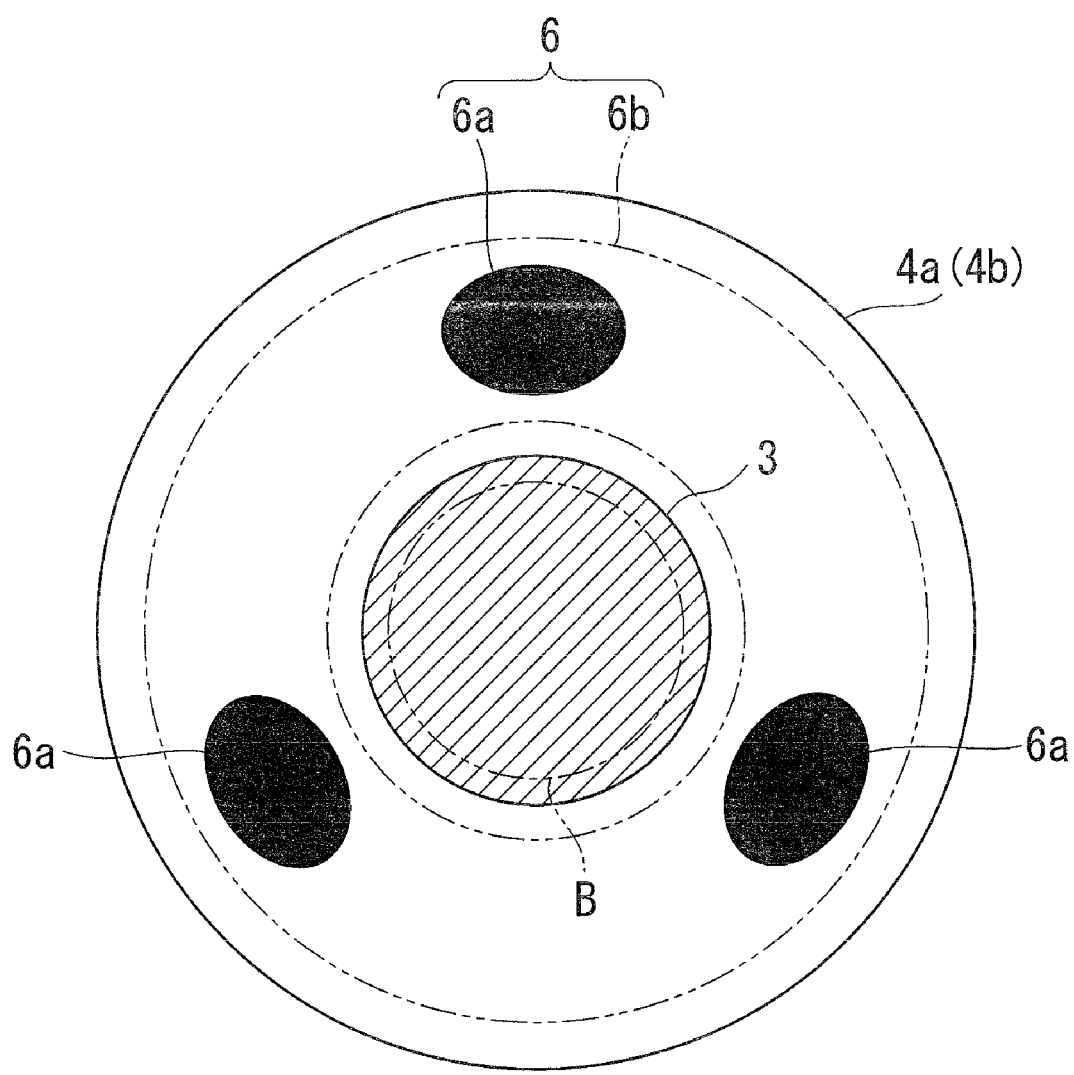
[FIG. 5]

As shown in FIG. 5, for three sensor electrodes 6a provided with gaps therebetween in the circumferential direction of one optical substrate 4a, a single sensor electrode 6b with a size that opposes all three of these sensor electrodes 6a may be provided on the other optical substrate 4b.

In this case, if three of the sensor electrodes 6a are provided on one optical substrate 4a, it is possible to obtain three detection signals, making it possible to obtain the minimum required information for detecting the tilt error of the optical substrates 4a and 4b when driving the actuators. Accordingly, it is possible to adjust the parallelism between the optical substrates 4a an 4b, and the gap between the two optical substrates 4a and 4b can be precisely controlled, which makes it possible to spectrally separate light in a desired wavelength band with superior precision.

The shapes of the sensor electrodes 6a and 6b are not particularly limited; it is possible to employ any shape, such as an elliptical shape like the sensor electrodes 6a shown in FIG. 5, a pie wedge shape like the sensor electrodes 6b shown in FIG. 3 or FIG. 4, or a rectangular shape.

In the variable spectroscopy element 1 according to this embodiment, a sensor of the electrostatic capacitance type is employed as the sensor 6 for detecting the gap between the optical substrates 4a and 4b, and the sensor electrodes 6a and 6b are provided in the outer peripheral portions of the optical substrates 4a and 4b. Instead of this, an eddy-current type sensor may be employed as the sensor for detecting the gap between the optical substrates 4a and 4b. More specifically, instead of the sensor electrodes described in the above embodiment, it is possible to employ a configuration in which sensor coils for generating eddy currents are provided at the outer peripheral portions of the respective optical substrates 4a and 4b, and the gap between the optical substrates 4a and 4b is measured on the basis of the inductances (the level of which changes according to the distance between the opposing sensor coils) detected by these sensor coils.

In this embodiment, the reflective films 3 provided on the opposing surfaces of the optical substrates 4a and 4b may be formed of conductive material, and the reflective films themselves may serve dual purpose as the sensor electrodes 6a and 6b forming the electrostatic capacitance.

Next, an endoscope system 10 according to an embodiment of the present invention will be described with reference to FIGS. 6 to 9.

Figure 6:
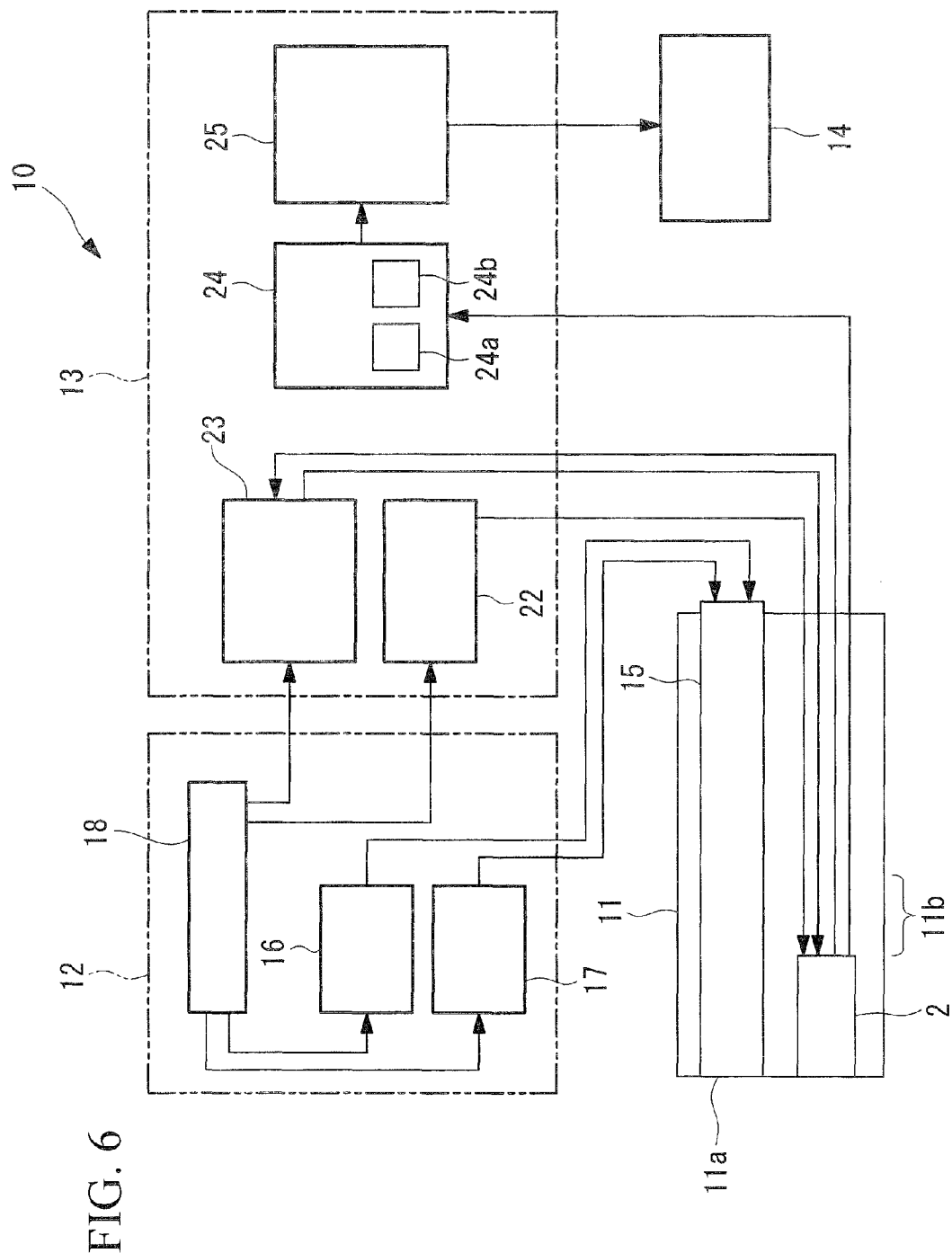
[FIG. 6]

As shown in FIG. 6, the endoscope system 10 according to this embodiment includes an insertion portion 11 that is inserted inside the body cavity of a living organism, an image-acquisition unit 2 that is disposed inside the insertion portion 11, a light source unit 12 that emits multiple types of light, a control unit 13 that controls the image-acquisition unit 2 and the light source unit 12, and a display unit 14 that displays an image acquired by the image-acquisition unit 2.

The insertion portion 11 has extremely narrow outer dimensions allowing it to be inserted into the body cavity of the living organism. The insertion portion 11 is provided, in the interior thereof, with the image-acquisition unit 2 and a light guide 15 that conveys light from the light source unit 12 to a distal end 11a.

The light source unit 12 includes an illumination-light light source 16 that emits illumination light that illuminates an observation object A inside the body cavity, for obtaining reflected light that returns upon reflection at the observation object A; an excitation-light light source 17 that emits excitation light that is radiated onto the observation object A inside the body cavity, for generating fluorescence upon exciting a fluorescent substance present inside the observation object A; and a light-source control circuit 18 that controls these light sources 16 and 17.

The illumination-light light source 16 is, for example, a combination of a xenon lamp and a bandpass filter, which are not illustrated, and the 50% transmission band of the bandpass filter is 430 nm to 460 nm. In other words, the light source 16 generates illumination light in a wavelength band of 430 nm to 460 nm.

The excitation-light light source 17 is, for example, a semiconductor laser that emits excitation light with a peak wavelength of 660±5 nm. Excitation light with this wavelength can excite a fluorescent agent such as Cy5.5 (formerly manufactured by Amersham, currently GE Health Care Inc.) or Alexafluor700 (manufactured by Molecular Probes).

The light-source control circuit 18 alternately turns on and off the illumination-light light source 16 and the excitation-light light source 17 at a prescribed timing according to a timing chart to be described later.

The image acquisition unit 2 is disposed in an end portion of the insertion portion 11.

As shown in FIG. 1, the image-acquisition unit 2 is provided with an image-acquisition optical system 19 including lenses 19a and 19b that collect light incident from the observation object A, an excitation-light cut filter 20 that blocks excitation light incident from the observation object A, the above-described variable spectroscopy element 1, whose spectral characteristics can be changed by the operation of the control unit 13, an image-acquisition device 21 that captures the light collected by the image-acquisition optical system 19 and converts it to an electrical signal, and a frame member 5 that supports these parts.

Figure 7:
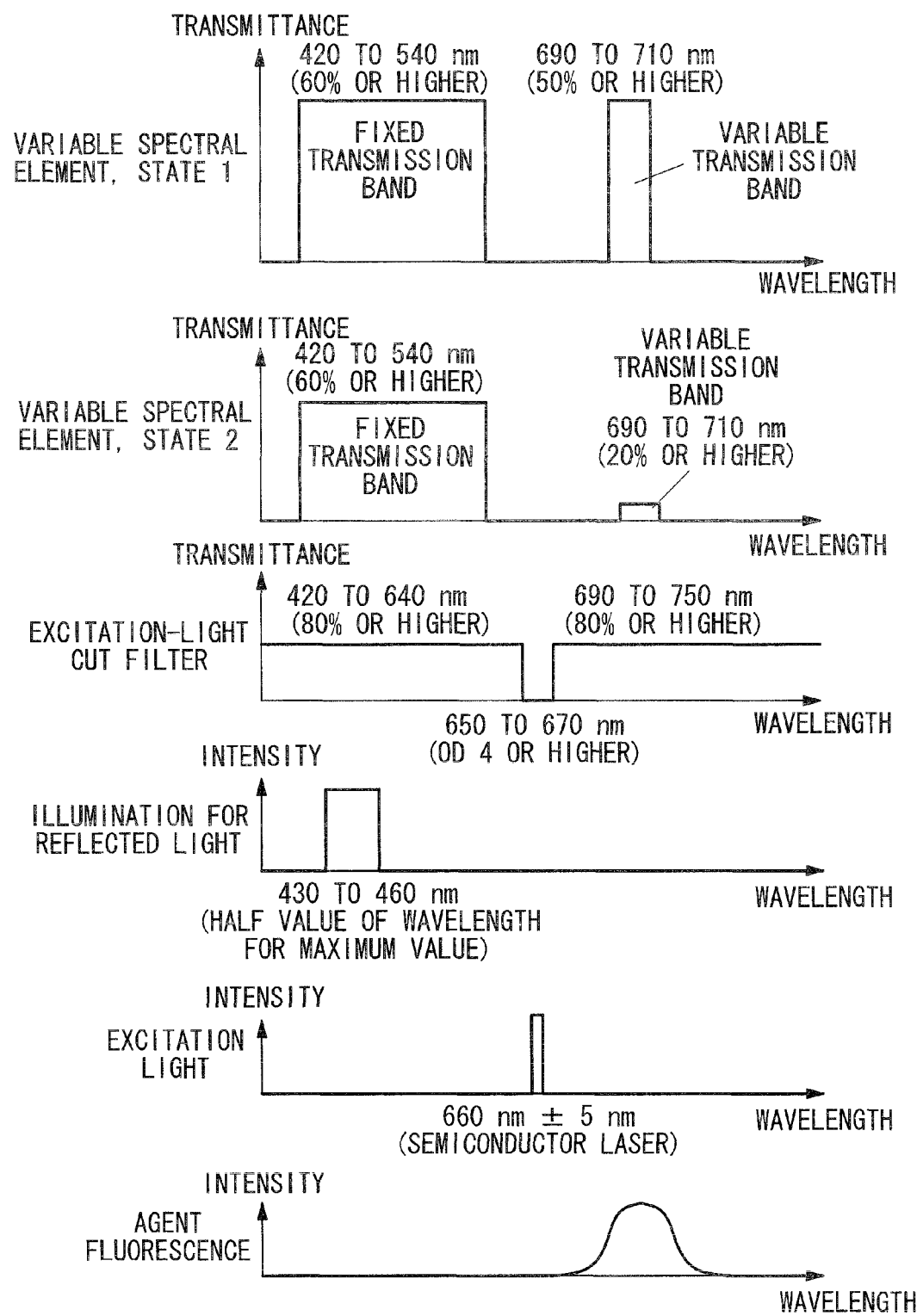
[FIG. 7]

More specifically, as shown in FIG. 7, the variable spectroscopy element 1 has a transmittance-wavelength characteristic having two transmission bands: one fixed transmission band and one variable transmission band. The fixed transmission band always transmits the incident light, regardless of the state of the variable spectroscopy element 1. In the variable transmission band, the transmittance characteristic changes depending on the state of the variable spectroscopy element 1.

Figure 9:
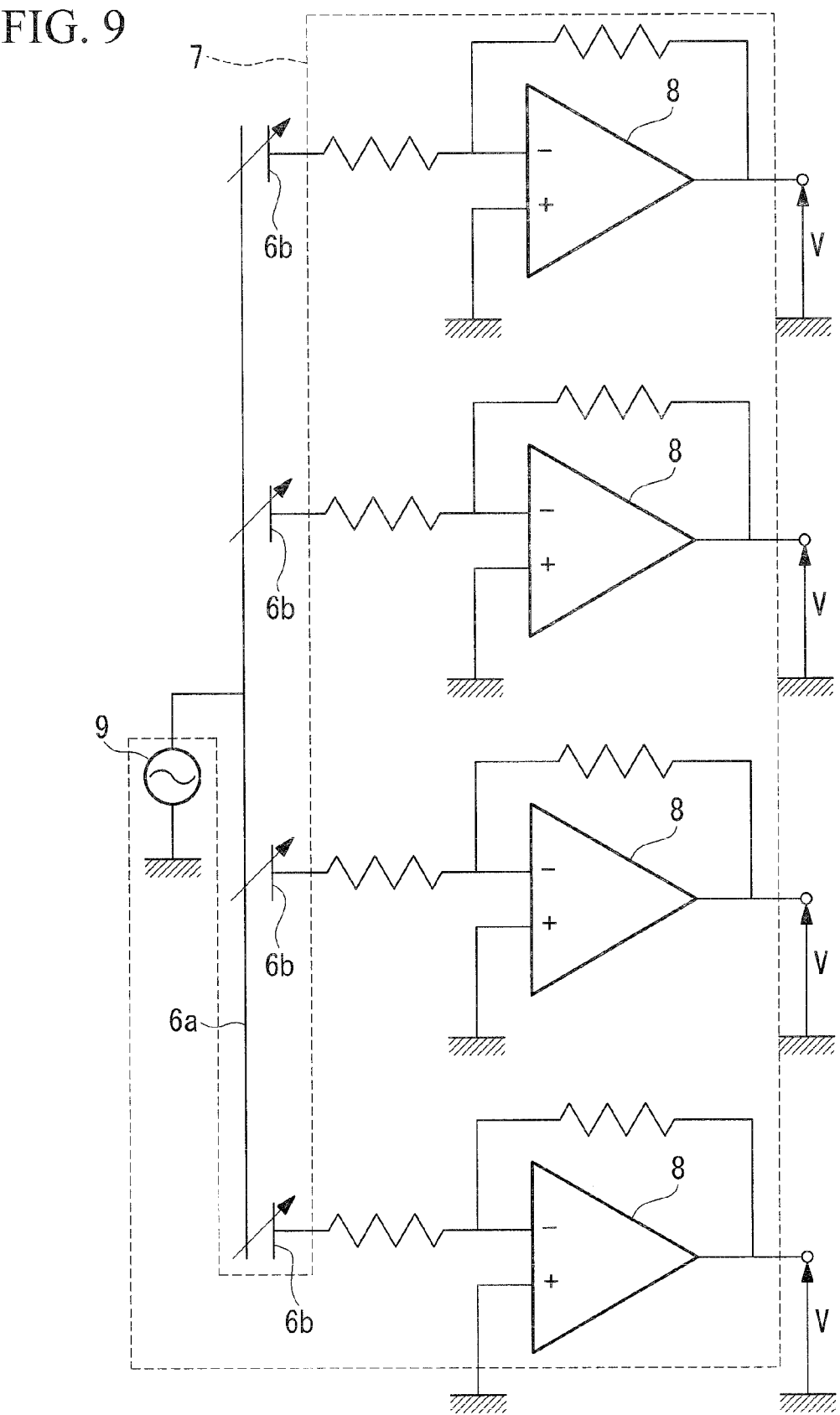
[FIG. 9]

An electrical circuit 7 such as that shown in FIG. 9, for example, is connected to the sensor electrodes 6a and 6b. The electrical circuit 7 supplies an AC current to the sensor electrodes 6a and 6b, converts the electrostatic capacitances between the sensor electrodes 6a and 6b, which are determined according to the distance between the optical substrates 4a and 4b, to electrical signals, amplifies them, and outputs them (voltages V). In FIG. 9, the members indicated by reference sign 8 are operational amplifiers, which are active elements, and the member indicated by reference sign 9 is an AC power supply. The electrical circuit 7 is secured to the optical substrate 4a, which is secured to the frame member 5.

As shown in FIG. 6, the control unit 13 includes an image-acquisition-device driving circuit 22 that drive controls the image-acquisition device 21, a variable-spectroscopy-element control circuit 23 that drive controls the variable spectroscopy element 1, a frame memory 24 that stores image information acquired by the image-acquisition device 21, and an image processing circuit 25 that processes the image information stored in the frame memory 24 and outputs it to the display unit 14.

The image-acquisition-device driving circuit 22 and the variable-spectroscopy-element control circuit 23 are connected to the light-source control circuit 18 and drive control the variable spectroscopy element 1 and the image-acquisition device 21 in synchronization with the switching of the illumination-light light source 16 and the excitation-light light source 17 by the light-source control circuit 18.

Figure 8:
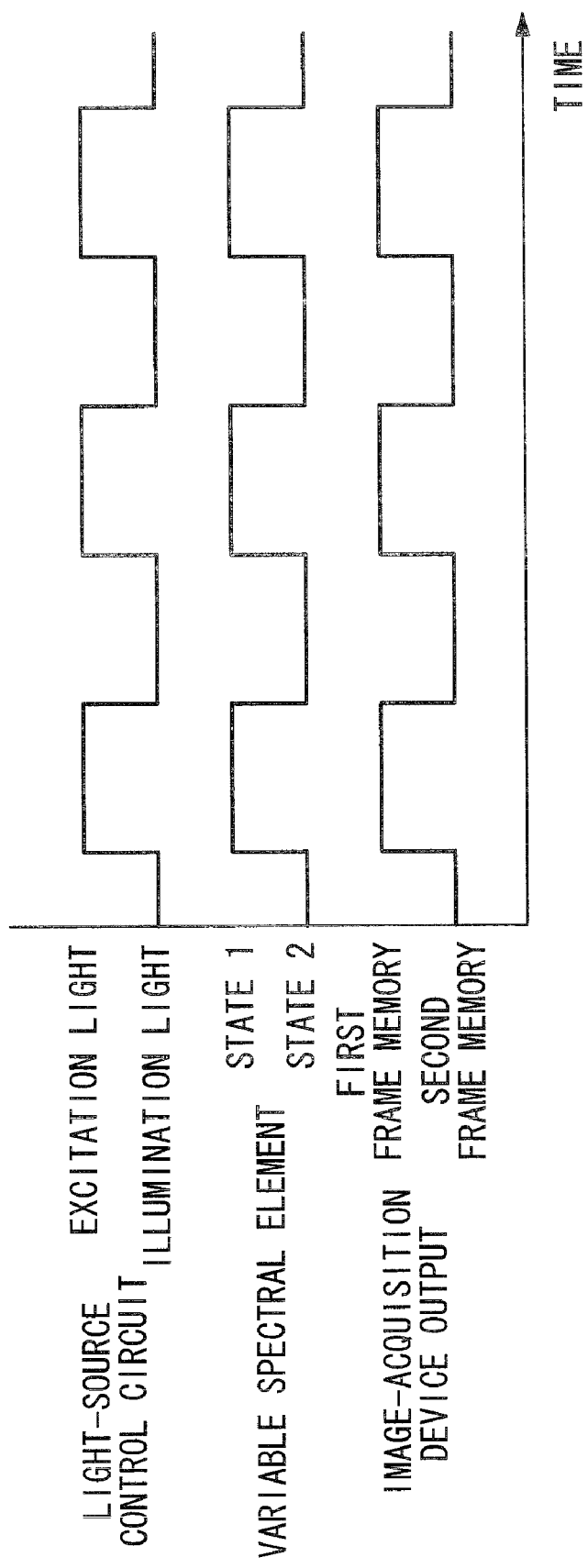
[FIG. 8]

More specifically, as shown in the timing chart in FIG. 8, when excitation light is emitted from the excitation-light light source 17 by the operation of the light-source control circuit 18, the variable-spectroscopy-element control circuit 23 places the variable spectroscopy element 1 in the first state, and the image-acquisition-device driving circuit 22 outputs the image information output from the image-acquisition device 21 to the first frame memory 24a. When illumination light is emitted from the illumination-light light source 16, the variable-spectroscopy-element control circuit 23 places the variable spectroscopy element 1 in the second state, and the image-acquisition-device driving circuit 22 outputs the image information output from the image-acquisition device 21 to the second frame memory 24b.

The image processing circuit 25 receives from the first frame memory 24a the fluorescence image information obtained by radiating the excitation light and outputs it on a first channel of the display unit 14, and receives from the second frame memory 24b the reflected-light image information obtained by radiating the illumination light and outputs it on the second channel of the display unit 14.

The operation of the thus-configured endoscope system 10 according to this embodiment will be described below.

To capture an observation object A inside the body cavity of a living organism using the endoscope system 10 according to this embodiment, a fluorescent agent is injected into the body, and the insertion portion 11 is inserted inside the body cavity so that the distal end 11a thereof opposes the observation object A inside the body cavity. In this state, the light source unit 12 and the control unit 13 are activated, and by operating the light-source control circuit 18, the illumination-light light source 16 and the excitation-light light source 17 are alternately operated to respectively generate illumination light and excitation light.

The excitation light and the illumination light generated in the light source unit 12 are both propagated to the distal end 11a of the insertion portion 11 via the light guide 15 and are radiated from the distal end 11a of the insertion portion 11 towards the observation object A.

When the excitation light is radiated onto the observation object A, the fluorescent agent present in the observation object A is excited, and fluorescence is generated. The fluorescence emitted from the observation object A is collected by the image-acquisition optical system 19 in the image-acquisition unit 2, passes through the excitation-light cut filter 20, and is incident on the variable spectroscopy element 1.

Because the variable spectroscopy element 1 is switched to the first state by the variable-spectroscopy-element control circuit 23 in synchronization with the operation of the excitation-light light source 17, the transmittance with respect to the fluorescence is increased, allowing the incident fluorescence to be transmitted therethrough. In this case, part of the excitation light radiated onto the observation object A is reflected at the observation object A and is incident on the image-acquisition unit 2 together with the fluorescence. However, because the image-acquisition unit 2 is provided with the excitation-light cut filter 20, the excitation light is blocked and is prevented from being incident on the image-acquisition device 21.

Thus, the fluorescence transmitted through the variable spectroscopy element 1 is incident on the image-acquisition device 21, and fluorescence image information is obtained. The obtained fluorescence image information is stored in the first frame memory 24a, is output on the first channel of the display unit 14 by the image processing circuit 25, and is displayed by the display unit 14.

On the other hand, when the illumination light is radiated onto the observation object A, the illumination light is reflected at the surface of the observation object A. This illumination light passes through the lens 19a and the excitation-light cut filter 20, and is incident on the variable spectroscopy element 1. Because the wavelength band of the reflected light of the illumination light is located in the fixed transmission band of the variable spectroscopy element 1, all of the reflected light incident on the variable spectroscopy element 1 is transmitted through the variable spectroscopy element 1.

Then, the reflected light transmitted through the variable spectroscopy element 1 is incident on the image-acquisition device 21, and reflected-light image information is obtained. The obtained reflected-light image information is stored in the second frame memory 24b, is output on the second channel of the display unit 14 by the image processing circuit 25, and is displayed by the display unit 14.

At this time, because the excitation-light light source 17 is off, fluorescence due to excitation light with a wavelength of 660 nm is not generated. Because the excitation efficiency with respect to the fluorescent agent is extremely low in the wavelength region of the illumination-light light source 16, it can be considered that effectively none is generated. In addition, because the variable spectroscopy element 1 is switched to the second state by the operation of the variable-spectroscopy-element control circuit 23 in synchronization with the operation of the illumination-light light source 16, the transmittance with respect to the fluorescence is reduced, so even though the fluorescence is incident, it is blocked. Accordingly, only the reflected light is acquired by the image-acquisition device 21.

Thus, with the endoscope system 10 according to this embodiment, it is possible to provide the user with a fluorescence image and a reflected-light image.

In this case, with the endoscope system 10 according to this embodiment, because the variable spectroscopy element 1 is provided with the sensor 6, when switching between the first state and the second state, the distance between the two optical substrates 4a and 4b is detected by the sensor 6, and the electrical signals applied to the actuators 4c are feedback controlled. Accordingly, the distance between the optical substrates 4a and 4b can be precisely controlled, light in a desired wavelength band can be spectrally separated with high precision, and a clear fluorescence image and reflected-light image can be acquired.

In this embodiment, because the number of sensors 6b provided on the optical substrate 4b positioned at the distal end 11a side of the insertion portion 11 is smaller than the number of sensors provided on the optical substrate 4a positioned at the base end, it is possible to reduce the number of wires at the distal end 11a side where there is less space. Accordingly, it is possible to reduce the diameter of the distal end 11a of the insertion portion 11, and it is possible to reduce the occurrence of crosstalk noise associated with the proximity of the wires.

In this embodiment, after the electrical signals output from the sensor electrodes 6a and 6b, indicating the electrostatic capacitance between the sensor electrodes 6a and 6b, are amplified by the electrical circuit 7 secured to the optical substrate 4a of the variable spectroscopy element 1, which reduces the output impedance, the are conveyed inside the insertion portion 11 and are sent from the base end of the insertion portion 11 to the variable-spectroscopy-element control circuit 23 outside the body. Therefore, it is possible to reduce the intrusion of noise on the electrical signals detected by the sensor 6, which allows the gap between the optical substrates 4a and 4b to be accurately detected, and as a result, an advantage is afforded in that it is possible to accurately control the spectral characteristics of the variable spectroscopy element 1.

In this embodiment, electrodes with different outer dimensions are employed as the sensor electrodes 6a and 6b provided on the opposing surfaces of each of the optical substrates 4a and 4b. Therefore, during driving of the actuators 4c in this embodiment, even in cases where a shift occurs between the optical substrates 4a and 4b in a direction intersecting the optical axis, due to individual differences etc. in the actuators 4c, the electrostatic capacitance formed between the opposing sensor electrodes 6a and 6b does not change, and it is possible to precisely detect the distance between the optical substrates 4a and 4b.

In the endoscope system 10 according to this embodiment, the element in any of FIGS. 1 to 5 may be used as the variable spectroscopy element 1.

In addition, although a circuit that detects the electrostatic capacitance as an electrical signal and amplifies it is used as the electrical circuit 7, the present invention is not limited to such a configuration; a buffer circuit having no amplification function may be used. Examples of buffer circuits include, for instance, voltage follower circuits. It is possible to reduce the output impedance of the sensor output even with a buffer circuit, and the noise-resistance can be improved.

In the endoscope system 10 according to this embodiment, a system that obtains an agent-fluorescence image and a reflected-light image has been described. Instead of this, however, the present invention can use another observation method, such as an observation method for performing observation by acquiring an autofluorescence image and an agent-fluorescence image, an observation method for performing observation by acquiring an autofluorescence image and a reflected-light image, or an observation method for performing observation by acquiring a reflected-light image alone.

Additionally, although a circuit that converts an electrostatic capacitance value into a voltage value is used as the electrical circuit 7 for the sensors 6, a circuit that converts it to an electrical current value may be used as the electrical circuit 7.

This embodiment has been described by illustrating the endoscope 10 having a bending portion 11b as an example. Instead of this, however, it may be applied to a rigid scope having no bending portion 11b, or it may be applied to a capsule endoscope. The observation object A in the invention of the present application is not limited to a living organism. The invention of the present application can also be applied to industrial endoscopes that target the interior of structural members etc.

In this embodiment, a description has been given of the endoscope system 10 in which the image-acquisition unit 2 is provided with the variable spectroscopy element 1. Instead of this, as shown in FIGS. 10 and 11, the invention of the present application may also be an endoscope system 33 in which the variable spectroscopy element 1 is provided in part of a light source unit 34 disposed at the distal end of the insertion portion 11.

Figure 11:
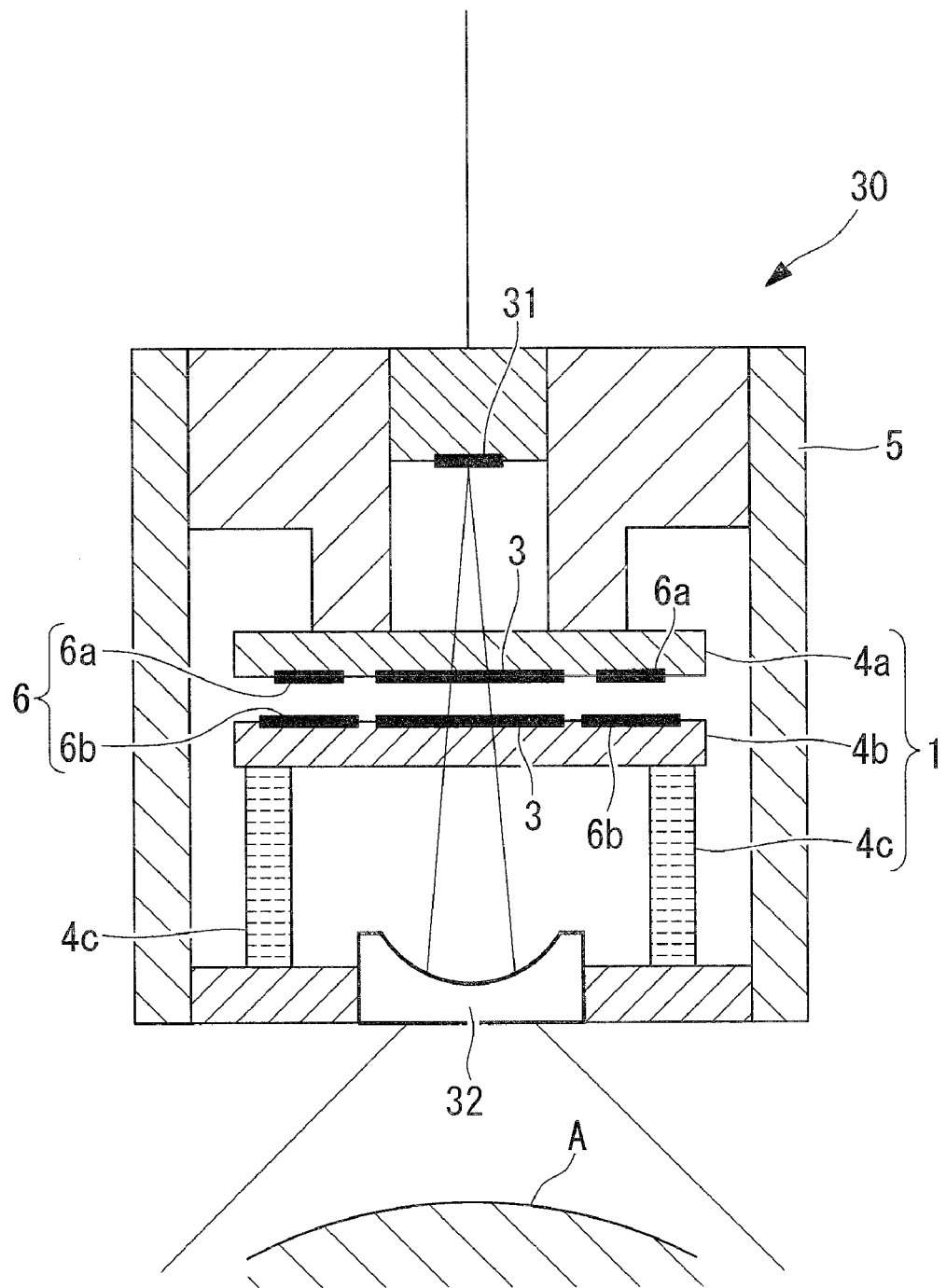
[FIG. 11]

As shown in FIG. 11, the light source unit 34 includes a distal-end light source 30 disposed at the end portion of the insertion portion 11 and a light-source controller 35 that is disposed outside the body and that controls the distal-end light source 30.

Figure 10:
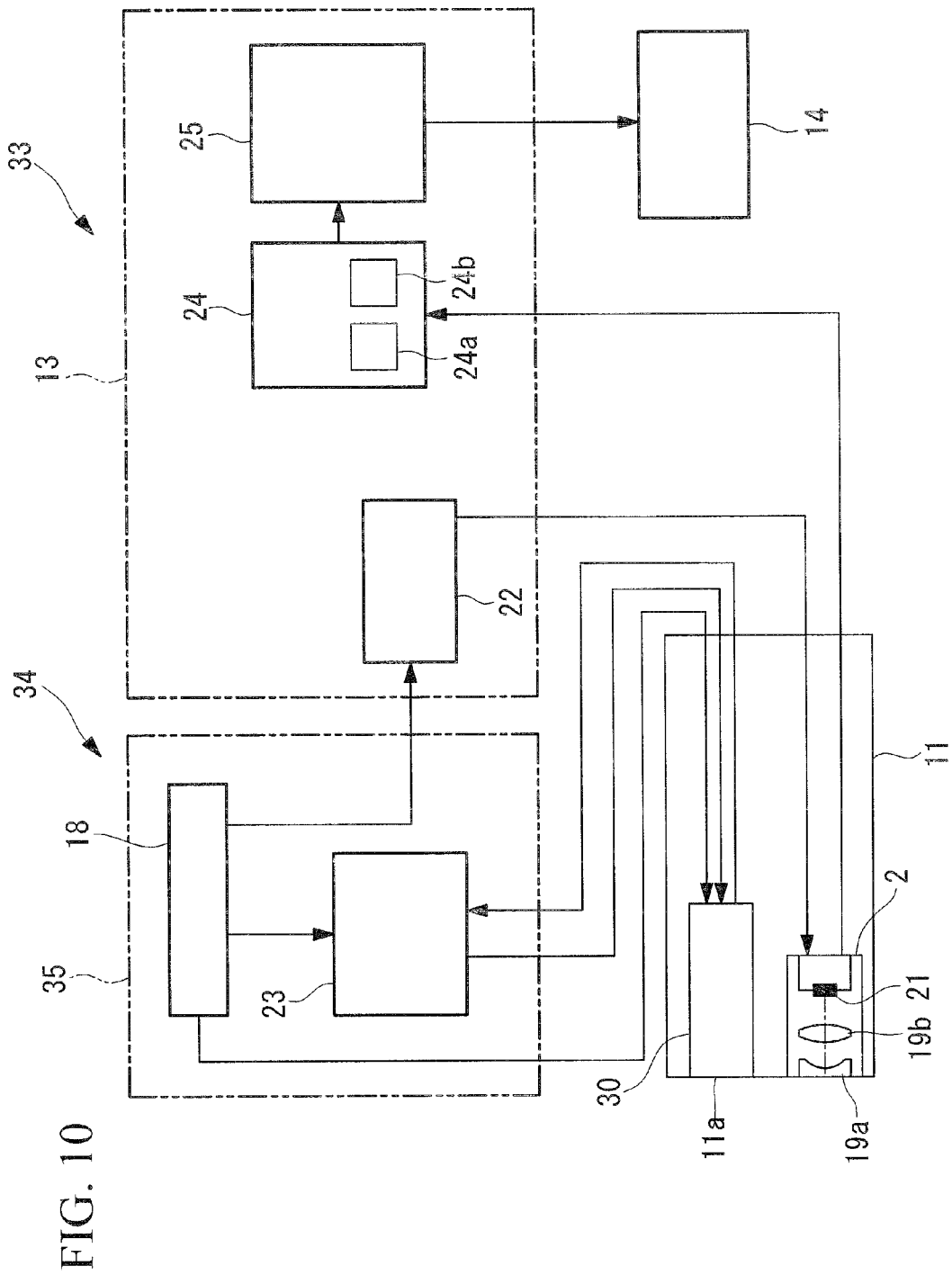
[FIG. 10]

As shown in FIG. 10, the distal-end light source 30 includes a white LED (photoelectric conversion device) 31 that generates white light; a variable spectroscopy element 1, which is formed of two optical substrates 4a and 4b and actuators 4c; a lens 32 that spreads the white light emitted from the white LED 31; and a frame member 5 to which these parts are secured.

Accordingly, as well as allowing a reduction in the diameter of the distal end of the insertion portion 11, it is also possible to reduce the number of wires, thus decreasing the intrusion of noise, and the distance between the optical substrates 4a and 4b is accurately detected, which allows the observation object A to be irradiated with illumination light in a wavelength band that is spectrally separated from the white light with superior precision.

Besides the case where a single white LED 31 is provided in the distal-end light source 30, a plurality of white LEDs 31 may be disposed in order to achieve increased illumination light level and improved light distribution characteristics. Also, it is possible to combine a single white LED 31 with a diffuser, or to use a lamp or device with increased surface area, etc.

Instead of the white LED 31, it is possible to use a multi-wavelength-excitation semiconductor laser, a superluminescent diode, etc. in the distal-end light source 30.

The invention claimed is:

1. A variable spectroscopy element comprising:
   first and second optical substrates that oppose each other with a gap there between;
   optical coating layers provided on opposing surfaces, which face each other, of the first and second optical substrates;
   an actuator that changes the gap between the first and second optical substrates;
   a number of first sensor portion portions provided on the first optical substrate for detecting the gap between the first and second optical substrates; and
   a number of second sensor portions provided on the second optical substrate so as to oppose the first sensor portions, for detecting the gap between the first and second optical substrates,
   wherein the numbers of the first and second sensor portions differ.

2. A variable spectroscopy element according to claim 1, wherein the number of first sensor portions is equal to or greater than the number of degrees of freedom of the actuator, and the number of second sensor portions is smaller than the number of first sensor portions.

3. A variable spectroscopy element according to claim 2, wherein the number of first sensor portions is equal to the number of degrees of freedom of the actuator.

4. A variable spectroscopy element according to claim 2, wherein the number of second sensor portions is one.

5. A variable spectroscopy element according to claim 1, wherein the number of first sensor portions is three or more.

6. A variable spectroscopy element according to claim 5, wherein the number of second sensor portions is one.

7. A variable spectroscopy element according to claim 2, wherein the first optical substrate is secured and the second optical substrate can be displaced by the actuator.

8. A variable spectroscopy element according to claim 7, wherein the number of second sensor portions is one.

9. A variable spectroscopy element according to claim 1, wherein the first and second sensor portions are sensor portions of the electrostatic capacitance type.

10. A variable spectroscopy element according to claim 1, wherein the first and second sensor portions are sensor portions of the eddy current type.

11. A spectroscopy apparatus comprising:
    a variable spectroscopy element according to claim 1; and
    an image-acquisition device that captures light spectrally separated by the variable spectroscopy element.

12. An endoscope system comprising the spectroscopy apparatus according to claim 11.

13. An endoscope system according to claim 12, wherein the variable spectroscopy element is provided in an insertion portion that is inserted inside a body cavity, and the second optical substrate is disposed farther toward the distal-end side of the insertion portion than the first optical substrate is.

* * * * *